United States Patent
Da Silva Rodrigues et al.

(10) Patent No.: US 9,770,603 B2
(45) Date of Patent: Sep. 26, 2017

(54) DETECTOR FOR RADIOTHERAPY TREATMENT GUIDANCE AND VERIFICATION

(71) Applicant: KONINKLIJKE PHILIPS N.V., Eindhoven (NL)

(72) Inventors: Pedro Jorge Da Silva Rodrigues, Veldhoven (NL); Andreia Maria Araujo Trinadade Rodrigues, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 76 days.

(21) Appl. No.: 14/893,948

(22) PCT Filed: Jun. 6, 2014

(86) PCT No.: PCT/EP2014/061771
§ 371 (c)(1),
(2) Date: Nov. 25, 2015

(87) PCT Pub. No.: WO2014/198644
PCT Pub. Date: Dec. 18, 2014

(65) Prior Publication Data
US 2016/0121139 A1    May 5, 2016

(30) Foreign Application Priority Data

Jun. 13, 2013   (EP) .................... 13171796

(51) Int. Cl.
*A61N 5/10* (2006.01)
*G01T 1/20* (2006.01)

(52) U.S. Cl.
CPC ......... *A61N 5/1049* (2013.01); *A61N 5/1071* (2013.01); *A61N 5/1077* (2013.01); *G01T 1/201* (2013.01); *A61N 2005/1054* (2013.01)

(58) Field of Classification Search
CPC ......... G01T 1/2018; G01T 1/20; G01T 1/202; G01T 1/247; G01T 1/2006; G01T 1/2928;
(Continued)

(56) References Cited

U.S. PATENT DOCUMENTS 6,215,848 B1   4/2001   Linders et al.
7,831,109 B2   11/2010  Maack
(Continued)

FOREIGN PATENT DOCUMENTS

JP   2000002768    1/2000
WO   00/29873      5/2000
WO   2010/057500   5/2010

OTHER PUBLICATIONS

El-Mohri, et al., "Low-dose megavoltage cone-beam CT imaging using thick, segmented scintillators", Phys. Med. Biol. 56 (2011) 1509-1527.
(Continued)

*Primary Examiner* — Hoon Song (57) ABSTRACT

The present invention relates a detector (11) for detecting megavoltage X-ray radiation (3), comprising a scintillator (2) including a plurality of heavy scintillating fibers (13) for emitting scintillation photons in response to incident megavoltage X-ray radiation (3), a support structure (15) for supporting said plurality of heavy scintillating fibers (13) and holding them in place; and a photodetector (17) for detecting the spatial intensity distribution of the emitted scintillation photons. The present invention further relates to an apparatus (35) for radiation therapy comprising a particle accelerator (37) and a detector (11) for detecting megavoltage radiation. Still further, the present invention relates to methods for detecting X-ray radiation and for radiation therapy.

20 Claims, 4 Drawing Sheets

(58) Field of Classification Search
CPC ... G01T 1/24; G01N 23/046; G01N 2223/505
See application file for complete search history.

(56) References Cited

U.S. PATENT DOCUMENTS

| | | | |
|---|---|---|---|
| 2004/0140431 A1* | 7/2004 | Schmand | G01T 1/2018 250/367 |
| 2005/0035294 A1 | 2/2005 | Leppert | |
| 2006/0202125 A1* | 9/2006 | Suhami | B82Y 20/00 250/368 |
| 2007/0164225 A1* | 7/2007 | Pang | G01T 1/22 250/367 |
| 2008/0061243 A1* | 3/2008 | Doshi | G01T 1/2018 250/368 |
| 2008/0128631 A1 | 6/2008 | Suhami | |
| 2012/0205530 A1 | 8/2012 | Beaulieu et al. | |
| 2012/0292517 A1 | 11/2012 | Izaguirre et al. | |

OTHER PUBLICATIONS

Auffray, et al., "Status of Heavy Scintillating Crystal Fibers for Calorimetry", Nov. 2008, CERN.

Wang, et al., "High-DQE EPIDs based on thick, segmented BGO and CsI:Tl scintillators: Performance evaluation at extremely low dose", Med. Phys. 36, Dec. 12, 2009.

Liu, et al., "Countering beam divergence effects with focused segmented scintillators for high DQE megavoltage active matrix imagers", Phys. Med. Biol. 57 (2012) 5343-5358.

Wang, et al., "Monte Carlo investigations of the effect of beam divergence on thick, segmented crystalline scintillators for radiotherapy imaging", Phys. Med. Biol. 55 (2010) 3659-3673.

Lecoq, "New approaches in scintillation detectors in the context of HEP calorimetry and medical imaging", CERN, SiPM workshop, Geneva, 2011.

Novotny, et al., "Frontier Scintillation Detectors Based on Inorganic Fibers", Sep. 2010.

Broderick, et al., "A comparison of kilovoltage and megavoltage cone beam CT in radiotherapy", Journal of Radiotherapy in Practice 6 (2007) 173-178.

SIEMENS, "In-Line kView Imaging", 2009, Order No. A91OCS-608-01-C1-7600.

Amer, et al., "Imaging doses from the Elekta Synergy X-ray cone beam CT system" British Journal of Radiology (2007) 80, 476-48.

Hansen, et al., "Image-guided radiotherapy using megavoltage cone-beam computed tomography for treatment of paraspinous tumors in the presence of orthopaedic hardware", Int. J. Radiation Oncology Biol. Phys., vol. 66, No. 2, pp. 323-326, 2006.

* cited by examiner

DETECTOR FOR RADIOTHERAPY TREATMENT GUIDANCE AND VERIFICATION

CROSS REFERENCE TO RELATED APPLICATIONS

This application is a national filing of PCT application Serial No. PCT/EP2014/061771, filed Jun. 6, 2014, published as WO 2014/198644 A1 on Dec. 18, 2014, which claims the benefit of European Application Number 13171796.9 filed Jun. 13, 2013, which is incorporated herein by reference.

FIELD OF THE INVENTION

The present invention relates to a detector and a corresponding method for detecting megavoltage X-ray radiation and to an apparatus and a corresponding method for radiation therapy. The present invention relates particularly to the detection of X-ray radiation generated by a medical linear particle accelerator and to image guided radiation therapy.

BACKGROUND OF THE INVENTION

One approach to cancer treatment is external beam radiotherapy or radiation therapy involving the treatment with a high intensity electron, photon, proton or hadron beam. In Image Guided Radiation Therapy (IGRT) the goal of maximizing the dose delivered to the tumor while minimizing the dose to surrounding tissue is enabled by information extracted from different imaging modalities and fed into the treatment planning and verification workflow.

Typically, more than 50% of all newly diagnosed cancer patients require external beam therapy as the main component of their treatment. Conventional external radiotherapy relies on radiation generated with a medical linear particle accelerator (LINAC) which, by means of a high intensity electron beam, produces either electron or photon treatment beams. Advances in linear accelerator techniques and controls have allowed the emergence of new treatment strategies like, e.g., Intensity-Modulated Radiation Therapy (IMRT) or volumetric-modulated arc therapy (VMAT), designed to maximize tumor control and to minimize damage to critical areas and healthy tissues. The potential clinical gains offered by the new treatment approaches can, however, be impaired by insufficient patient immobilization, set-up errors and verification at the time of treatment delivery. Occurrence of motion or tumor migration in relation to surrounding tissue make it necessary to include a step for treatment verification and treatment planning right before treatment.

In Image Guided Radiation Therapy with conventional photon beams two main techniques for beam monitoring and patient positioning have been introduced: megavoltage (MV) imaging using the same or a modified treatment beam (i.e. the radiation generated by the LINAC) or kilovoltage (kV) imaging using an additional X-ray beam. The LINAC energy spectrum ranges from the kilovoltage up to the megavoltage energy regime (end-point region around 6-18 MeV). Although most of the photons are in fact of energy less than 1 MeV, usually the terminology "megavoltage radiation" is used when referring to this type of radiation. In the context of this application, megavoltage X-ray radiation thus refers to energies in the kV and MV regime.

For many years megavoltage imaging using electronic portal devices (EPDI), either based on film or active matrix flat panel imagers (AMFPIs), was traditionally the main technique for geometric verification of field placement as well as dosimetric validation. However, verifying the position of a soft tissue target volume with megavoltage energy photons is challenging due to very small differences in the photon attenuation coefficient at these energies. In parallel to conventional 2D imaging, techniques for 3D imaging based on Cone Beam CT (CBCT) were also implemented. In the past solutions to improve the detection efficiency of AMFPIs by means of segmented heavy scintillator panels either in parallel of focused configurations have been proposed. However, these solutions usually come at the expense of degraded spatial resolution due to beam divergence.

As an alternative to MV electronic portal imaging, on-board kV imaging recently emerged as a way to improve the contrast of soft tissue and bones and is currently one of the main options for IGRT due to the prospect of enhanced localization of target volumes and adjacent organs at risk. Most commercial implementations rely on a kV X-ray source and an opposing amorphous silicon flat panel imager, mounted at 90° to the treatment head for the acquisition of kV X-ray projection images for radiography and fluoroscopy. The dose from a kV CBCT is lower than the dose from wide-field MV portal imaging, especially for anatomical sites where contrast is usually low requiring additional exposure time with MV beams. One example for such a detector is used in the Elekta Synergy system and relies on a $Gd_2O_2S$:Tb (GOS) screen readout by an amorphous silicon flat panel (RID 1604, Perkin-Elmer Optoelectronics). It has an active area of 41×41 $cm^2$ addressed as an array of 1024×1024 pixels, 400 micrometer pitch. The panel is located about half a meter from the axis of rotation and images are captured at a fixed frame rate of 2.7 Hz. Newer systems are being installed with a CsI panel, offering improved data acquisition at a higher frame rate.

In the Siemens Healthcare White Paper: "In-Line kView Imaging—The new standard in Image-Guided Radiation Therapy" an IGRT approach is presented which makes use of a modified treatment beam for imaging. The existing treatment beam is modified and optimized for imaging in order to provide kV-like images with high 2D and 3D soft tissue contrast using the on-board MV AMFPI device mounted on the LINAC gantry. For treatment purposes a flattening filter is used to achieve uniform dose across the field. This flattening filter absorbs low-energy photons, which are essential for high-contrast images. By removing this flattening filter for imaging purposes, the approach allows to utilize exactly those low-energy components in the beam. A beam of around 4 MV is typically used. In addition, the special carbon target used for imaging further shifts the energy spectrum toward the kV range which is more suitable for imaging. The modified beam can be detected with a regular flat panel detector. However, it is required to modify the beam for imaging.

In WO 2010/057500 A1 a radiation detector with doped optical guides is disclosed. The detector is suitable for use in connection with particle therapy applications and comprises at least one set of scintillating optical guides which upon exposure to incident radiation generate scintillating light. The optical guides are arranged in an array, such as in a so-called harp configuration, for detecting a transversal radiation beam profile.

In US 2012/0292517 A1 a radiation therapy system including a linear accelerator configured to emit a beam of radiation and a dosimeter configured to detect in real-time the beam of radiation emitted by the linear accelerator are disclosed. The dosimeter includes at least one linear array of scintillating fibers configured to capture radiation from the beam at a plurality of independent angular orientations, and a detection system coupled to the at least one linear array, the detection system configured to detect the beam of radiation by measuring an output of the scintillating fibers.

In US 2012/0205530 A1 a fluence monitoring detector for use with a multileaf collimator on a radiotherapy machine having an x-ray radiation source is disclosed. The fluence monitoring detector includes a plurality of scintillating optical fibers, a plurality of collection optical fibers coupled to the opposing ends of the scintillating optical fibers and a photo-detector coupled to the collection optical fibers.

In US 2007/0164225 A1 a Cerenkov x-ray detector for portal imaging is disclosed. The detector includes an optical-fiber taper (OFT) made from a large number of optical fibers. The optical-fiber taper is a matrix of optical fibers with the core material made of, e.g., silica and coated with a cladding glass or polymer. Each optical fiber in the optical fiber taper is fully aligned with the incident x-ray source so that x-rays entering the top of the fiber travel directly towards the bottom of the same fiber.

SUMMARY OF THE INVENTION

It is an object of the present invention to provide a detector and a corresponding method for detecting megavoltage X-ray radiation having improved detection efficiency, in particular for MV electronic portal imaging. It is further an object of the present invention to provide an apparatus for IGRT.

According to a first aspect of the present invention there is presented a detector for detecting megavoltage X-ray radiation, comprising a scintillator including a plurality of heavy scintillating fibers for emitting scintillation photons in response to incident megavoltage X-ray radiation, said plurality of heavy scintillating fibers pointing in the direction of a radiation source emitting the megavoltage X-ray radiation, a support structure for supporting said plurality of heavy scintillating fibers and holding them in place and a photo-detector for detecting the spatial intensity distribution of the emitted scintillation photons.

According to another aspect of the present invention, there is presented an apparatus for radiation therapy comprising a particle accelerator for generating megavoltage X-ray radiation, a subject support for supporting a patient or object being subject to treatment with radiation therapy by use of said megavoltage X-ray radiation and a detector for detecting megavoltage X-ray radiation as described herein.

According to further aspects of the present invention corresponding methods are presented. Preferred embodiments of the invention are defined in the dependent claims. It shall be understood that the claimed apparatus and methods have similar and/or identical preferred embodiments as the claimed detector and as defined in the dependent claims.

The detector according to the present invention is particularly suited for the detection of megavoltage X-ray radiation in comparison to other detectors that are mainly optimized for the detection of kilovoltage X-ray radiation. In this context, megavoltage X-ray radiation refers to the radiation generated by a LINAC, which can comprise photons with energies in the keV and MeV regimes. One feature of the detection of such radiation is that the detector comprises a scintillator which includes a plurality of heavy scintillating fibers. In the scintillator, i.e. in the scintillator material, scintillation photons are emitted in response to incident ionizing radiation, in particular X-ray radiation, megavoltage radiation or megavoltage X-ray radiation. Traditional scintillators used in the detection of X-ray radiation, in particular in medical imaging, make use of scintillation crystals, usually inorganic crystals, which may be arranged in a laminar structure, i.e. a planar, array or matrix of crystals. Different from such a laminar structure of crystals, according to the present invention heavy scintillating fibers are comprised in the scintillator. One advantage of this configuration is that it becomes possible to construct thicker scintillation structures. Thus, if the incident X-ray radiation is of high energy, i.e. megavoltage X-ray radiation, the amount of absorbed radiation can be increased. If a higher amount of radiation is absorbed, higher detection efficiency with respect to incident radiation can be achieved.

In the context of the present invention, heavy scintillating fibers preferably refer to inorganic fibers. However, it may also be possible to implement at least some of the advantages of the present invention by making use of plastic scintillating fibers, i.e. fibers comprising a plastic core material doped with fluorescent dopants such as BCF-10, BCF-12, BCF-20 (see e.g. "Comparison of BCF-10, BCF-12, and BCF-20 Scintillating Fibers for Use in a 1-Dimensional Linear Sensor"; Chichester, David L., IEEE 2012 Nuclear Science Symposium, 2012).

In order to keep the scintillating fibers in place in relation to one another and to the photodetector, the detector comprises a support structure which allows arranging the fibers in an ordered array or surface structure permitting incident X-ray radiation to enter into the fibers.

Further, the detector comprises a photodetector, which allows detecting scintillation photons emitted by the heavy scintillating fibers and deriving therefrom the intensity distribution of these scintillation photons (spatial intensity distribution). If, e.g., the fibers are supported in an array or matrix structure, then each fiber can be coupled to a photosensitive element in the photodetector and the intensity distribution detected by the photodetector is equivalent to the intensity distribution of the incident X-ray radiation.

In an embodiment the support structure comprises openings for inserting at least one end of the heavy scintillating fibers. Thus, the fibers are held in place and cannot move versus one another, versus the support structure or versus the photodetector. These openings or holes preferably have a diameter in the same range as the diameter of a heavy scintillating fiber or a bundle of heavy scintillating fibers. Preferably, a laminar support structure comprises a matrix array of openings in the form of cylinder shaped holes in the support structure and with varying angles versus the support structure so that each hole (and thus the inserted scintillating fiber) points in the direction of the radiation source. Direct or almost direct orientation of the fibers versus the radiation source allows a maximum amount of radiation to be captured. The other side of the scintillating fibers is directed towards the photodetector where it can be detected at which position (in particular in which heavy scintillating fiber) the scintillation event, i.e. the conversion of an incident X-ray to a scintillation photon, took place. The openings could be of various lengths (or depths), for example being as long as the whole scintillating fiber.

The support structure can be designed in different forms. One possibility is to design the support structure such that it allows directly connecting or attaching the scintillating fibers to the photodetector, e.g. by providing a mechanical coupling component between support structure and photodetector. One possible form of the support structure is a large planar or laminar structure, for example 400×400 mm$^2$, which can be read out by an appropriate 2D photosensor. For example, if a 2D photodetector array is used, each scintillating fiber can be connected to a single photodetector element. Alternatively, light sharing is possible, i.e. the scintillation photons from one fiber can reach multiple photodetector elements. Also other forms are possible, e.g. a focal form which provides openings such that heavy scintillating fibers inserted into the openings are in focus arrangement while the other side of the support structure is plain and can be easily coupled to a photodetector, e.g. a photodetector array or to another optical structure which allows determining which scintillating fiber was the source of a scintillation photon. It is also possible is to use additional connection means for connecting the photodetector to the fibers.

In comparison to scintillation crystals, heavy scintillating fibers can be easily arranged in a focus arrangement such that all fibers are oriented towards a single focus point. This focus point can e.g. be the X-ray radiation source. This individual orientation of each heavy scintillating fiber or each bundle of fibers is possible by making use of a support structure providing openings for fixating the fibers, which are pointing to the focus point. Thus, single fibers, arrays of fibers or bundles of fibers inserted in these openings are oriented towards this focus point. This embodiment allows using comparably long scintillating fibers and thereby obtaining high detection efficiency. Either bundles of scintillating fibers can be jointly kept in place by the support structure or each scintillating fiber can be separately held by the support structure and arranged in an array. Both possibilities allow focusing the single fibers or the fiber bundles to one focus point, which can, however, not only be a single-point source but also a spherical volume at a distance of the scintillator. One advantage of arranging the scintillating fibers in bundles or in an array is that a clearer assignment of specific scintillating fibers to photodetector positions or photodetector elements can be made.

According to one embodiment of the present invention the heavy scintillating fibers comprise an inorganic Z-effective material, in particular Ce-doped Lutetium Yttrium Orthosilicate, LSO/LYSO, Ce-doped or Pr-doped Lutetium Aluminum Garnet, LuAG:Ce/LuAG:Pr, Ce-doped Yttrium Aluminium Perovskite, YAP:Ce, Ce-doped Yttrium Orthosilicate, YSO:Ce, Tl-doped Cesium Iodide, CsI:Tl, Bismuth Germanate, PWO, BGO or GAGG:Ce in single crystal or ceramic formulations and loaded or unloaded with rare-earth materials like Lutetium.

A Z-effective or high-Z material in this context preferably refers to a high density material ($>5$ g/cm$^3$) comprising atoms with a high Z-number ($>50$). Inorganic Z-effective materials are particularly suited to be manufactured in the micropulling-down method allowing the efficient manufacturing of fibers. An alternative option for manufacturing such inorganic scintillating fibers is ceramic molding, a technique very suitable for ceramic garnet scintillators like GAGG and Lutetium doped derivatives. Another advantage of using such materials is that several of these crystals are capable of withstanding the radiation dose from a treatment photon beam, i.e. a megavoltage beam or a high energy beam, without losses in light transmission or other properties over a longer period due to induced radiation damage. This period can be up to ten years. Currently, micropulling-down technology allows growing Z-effective scintillating fibers, i.e. scintillating fibers consisting of materials with high-Z numbers, with an active length of up to 200 mm and a diameter between 0.3 to 3 mm.

In another embodiment the support structure also comprises a reflective material in between the heavy scintillating fibers and/or on the inner surface of the openings. This reflective material has the effect that scintillation photons generated in a scintillating fiber are kept to this fiber and do not leak to a neighboring fiber. It is also prevented that the emitted scintillation photons leave the fiber and do not reach the photodetector. Such leakage may result in a loss of light collection efficiency.

One possibility is to construct the support structure from a reflective material and to embed the scintillating fibers in this reflective material such that the scintillation photons are reflected back into the fiber in which they were generated. Another possibility is to only deposit a reflective material on the inner surface of the openings in the support structure which hold the scintillating fibers in place or even to deposit a reflective material on the scintillating fibers themselves.

In another embodiment the detector further comprises a reflector covering the heavy scintillating fibers, in particular a reflective material deposited over the heavy scintillating fibers or a plastic or metallic plate being placed over the fibers on which a reflective material is deposited. This reflective material covers the side of the scintillating fibers directed to the radiation source. Apart from the reflective material in between the heavy scintillating fibers as described above, it is also advantageous to cover the heavy scintillating fibers with a reflective material to prevent scintillation photons from leaking out of the scintillating fibers on the entrance side of the incident X-ray radiation. If an X-ray hits the scintillating fiber and the emission of a scintillation photon is triggered, this scintillation photon cannot only leak out of the fibers in radial direction, i.e. migrate to a neighboring fiber, but also in axial direction on the side of the scintillating fiber directed to the incident X-ray radiation. This is prevented by additionally using a reflective layer deposited over the scintillating fibers. It is desired to have as many scintillation photons as possible leaving the scintillating fiber on the side of the photodetector for obtaining high detection efficiency. One possibility for this is to use a reflective material on the radial sides of the fibers along with a reflector covering the heavy scintillating fibers on their axial side directed to the X-ray radiation source. It is advantageous if this reflector or reflective material is as transparent as possible for the incident X-ray radiation.

According to another embodiment the detector further comprises an optical layer arranged in between the heavy scintillating fibers and the photodetector for conducting the emitted scintillation photons from the heavy scintillating fibers to the photodetector. The main purpose of this additional optical layer is to allow using differently shaped photodetectors with the scintillating fibers. By providing an optical layer various forms of scintillating fibers and/or support structures can be combined with various forms of photodetectors. In particular, differences in size can be compensated.

In one embodiment this optical layer comprises optical fibers or optical-class transparent fibers. These fibers can be flexible for allowing a flexible connection of the heavy scintillating fibers with the photodetector. Alternatively, other types of optical fibers are possible, such as stiff fibers or plastic wavelength shifting fibers that are not loaded with a scintillator compound but with a wavelength shifting compound that absorbs the scintillation photons and re-emits light in another part of the spectrum (usually blue light is absorbed and green light is re-emitted) more suitable to the spectrum response (quantum efficiency) of the photosensor. It is particularly advantageous to connect each of the heavy scintillating fibers with a single optical fiber or flexible optical-class transparent fiber by means of light-conducting glue. Such a hybrid construction with each scintillating fiber optically coupled with light conducting glue to a flexible optical fiber has the additional advantage that the connection with the photodetector is facilitated.

In another aspect of the present invention, there is presented, as already mentioned above, an apparatus for radiation therapy, in particular for image guided radiation therapy. Preferably, the same radiation is used for imaging and therapy, i.e. treatment of an object or patient, so that the radiation source needs not to be modified or even exchanged between imaging and treatment.

It is further possible that the apparatus additionally comprises beamforming means for expanding or focusing the generated megavoltage X-ray radiation in order to pass through a larger or smaller area of the patient or object on the subject support. Still further, the apparatus may allow exchanging the high-Z bremsstrahlung target for a low-Z target (e.g. carbon) and thereby generating an optimized imaging beam based on the same particle accelerator. This beam can then also be detected by the detector according to the present invention but is usually not suitable for therapy due to too low energy.

In one embodiment of the apparatus according to the present invention the apparatus is configured for simultaneous treatment and detection by use of the same megavoltage X-ray radiation. When a treatment of a patient or object on the subject support is performed by a beam of megavoltage X-ray radiation, the detector can simultaneously detect portions of said megavoltage X-ray radiation that are transmitted through the patient or object and reach the detector. Thus, in comparison to other devices, which use a separate imaging modality, e.g. an on-board X-ray imager, or change the X-ray source to perform either treatment or detection, the apparatus according to the present invention allows simultaneously treating the patient and generating images from detected radiation in order to confirm that the treatment beam is guided to the desired area or volume in the patient and to correct the settings if necessary. One advantage of this embodiment is that no extra radiation dose has to be used besides the one used in the treatment itself.

In another embodiment of the apparatus, the particle accelerator is configured to generate (short) pulses of megavoltage X-ray radiation delivering a radiation dose lower than a treatment dose to a patient or object on the subject support and the detector is configured to detect said (short) pulses of megavoltage X-ray radiation. If, e.g., it is not desired to simultaneously treat the patient or object and generate images but it is rather desired to only generate an image, the apparatus allows generating an image based on short pulses which are also generated by the same radiation source, i.e. the particle accelerator, but which have lower energy than a usual treatment beam. One possible scenario where an image is needed could, e.g., be for the initial positioning of the patient or object on the subject support. Once the correct position is established and verified the treatment can start. During treatment position variations of the patient or object can be observed by simultaneously generating images from the detected megavoltage X-ray radiation. Another advantage is that the treatment does not have to be interrupted for image generation, e.g. in case the patient or object has changed its position. Further, security reasons may require to periodically assure that the treatment is still applied to the desired volume in the patient or object. Finally, the radiation source needs not to be modified or exchanged, albeit the radiation dose for the patient is reduced.

A further advantage is that, by making use of the same radiation for imaging and treatment, no additional particle accelerator or other radiation generation device is needed. Thus, the overall costs of such an apparatus can be reduced.

The megavoltage X-ray radiation, particularly for the use in medical radiation therapy, is preferably generated by a particle accelerator, particularly by a medical linear particle accelerator (LINAC). The generated X-ray radiation passes through a patient or object being subject to treatment with radiation therapy. For this, this patient or object is supported by a subject support which allows holding the patient or object in a certain position, i.e. treatment position. After passing through the patient or object, the radiation is detected by a detector as described above. In radiation therapy, especially in image guided radiation therapy, it is important to direct the treatment radiation, i.e. the treatment beam, to the specific area or volume in the object or patient being subject to treatment during the whole duration of the treatment. One task of the subject support is to keep the patient or object in the same position during the whole treatment. In comparison to other apparatuses for radiation therapy, the apparatus according to the present invention allows generating images of the patient or object on the subject support while being subjected to treatment.

The megavoltage X-ray radiation may be emitted in form of an expanded beam, i.e. a beam that passes through a larger volume of the patient or object on the subject support, so that an image of a larger area can be generated. The megavoltage X-ray radiation may alternatively be emitted in form of a focused beam, so that the dose delivered to a specific area or volume in the patient or object subjected to radiation therapy can be increased.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

One of the main concerns involving IGRT techniques is the extra dose the patient is subject to as a result of repeated or serial use of kV, MV CBCT or portal imaging. Currently the CT imaging procedure requires acquiring several image sequences for radiotherapy planning Together with the associated MV verification imaging procedure, this involves absorbed doses in various critical structures of 1-40 mGy for the CT imaging phase and 10-20 mGy for the verification phase. On the other hand CBCT in IGRT allows obtaining an image of the patient at every fraction in order to support set-up and visualization of the target/organs at risk. One of the problems with this approach is that a typical kV CBCT imaging protocol, e.g. for example in the pelvis region, can led to a patient surface dose of 30 mGy per scan. In the case of an online correction protocol or clinical studies/therapies that require imaging on a daily basis (40 fractions), the total surface dose can be over 2 Gy, i.e. already above the threshold for skin level radiation induced lesions.

Therefore and due to concerns with the extra dose involved in IGRT procedures with kV and MV on-board imaging, techniques to lower the total dose required for soft-tissue visualization at low dosage are needed. However, in the MV regime, conventional MV AMFPIs offer very low quantum efficiency (DQE) of a few percent (2-3%) of the radiation beam intensity. This is a consequence of the limited X-ray attenuation of the X-ray detector at MV energies (e.g. 6 MV). Such detectors typically consist of a 1 mm thick Cu plate and a $Gd_2O_2S$:Tb or CsI screen. At higher photon beam energies (up to 15-20 MV) the DQE gets even further reduced.

Improving the very low quantum efficiency in MV AMF-PIs could therefore result in major improvements on the imaging performance, dose reduction, and improved soft-tissue visualization with MV cone beam computed tomography (MVCT) performed at clinically acceptable doses.

FIG. 1 illustrates possible approaches to solve this problem. As shown in FIG. 1a, a segmented scintillator 1 can be used to detect the incident X-ray radiation 3 from a radiation source 5. The scintillator 1 consists of a two-dimensional matrix of high-aspect ratio elements in the form of scintillating crystals 7 separated by a septal wall material limiting the optical spread of the scintillation. Such improvements could enable the acquisition of high-quality portal images at very low doses, down to one beam pulse per image. However, as illustrated in FIG. 1b, this technique has the disadvantage that increasing the DQE is only possible by increasing the thickness of each pixel 7 in the segmented scintillator 1, which can introduce a severe blurring due to the diverging nature of the incident photon beam.

Figure 1A:
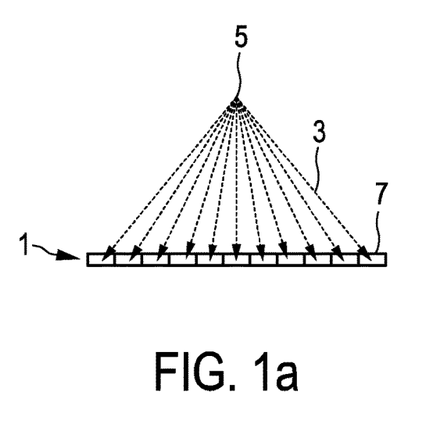
FIG. 1 shows different crystal scintillator arrangements for MV imaging.
Figure 1B:
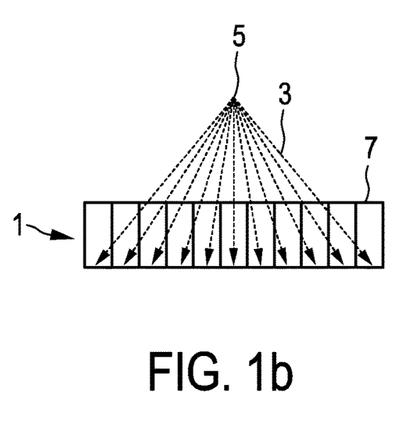
Figure 1C:
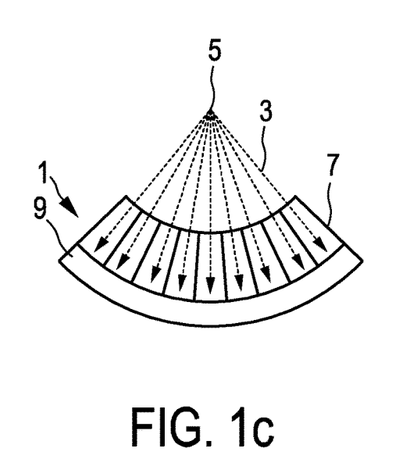
Figure 1D:
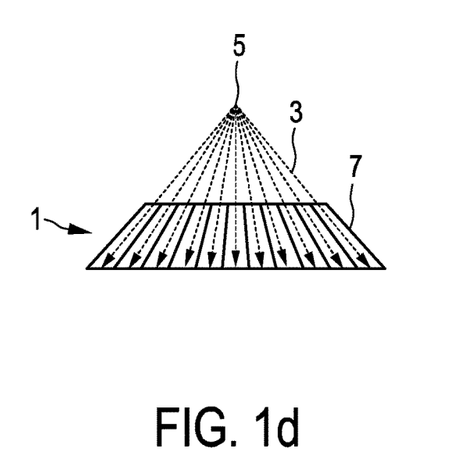

Two solutions could help to bypass this limitation. As illustrated in FIG. 1c, the scintillator pixels 7 can be placed over a flexible structure 9 oriented towards the emission point. Alternatively, as illustrated in FIG. 1d, different sized trapezoidal scintillation crystals 7 can be used. The main drawback is that either an efficient optical coupling strategy to transport the optical signal from the crystal elements to the photosensor array or a large number of different shaped crystals in order to maintain the detector focused with the incident beam is needed. Both approaches therefore usually result in high manufacturing costs of the sensor.

The solution to these problems proposed according to the present invention is the use of heavy, i.e. high-Z material, scintillating fibers arranged in either planar or focus arrangement. One advantage of this approach is that the radiation dose delivered to the patient can be reduced since long fibers with DQE>10% can be used without suffering from focal aberration effects that affect solutions like the one shown in FIG. 1b.

Figure 2:
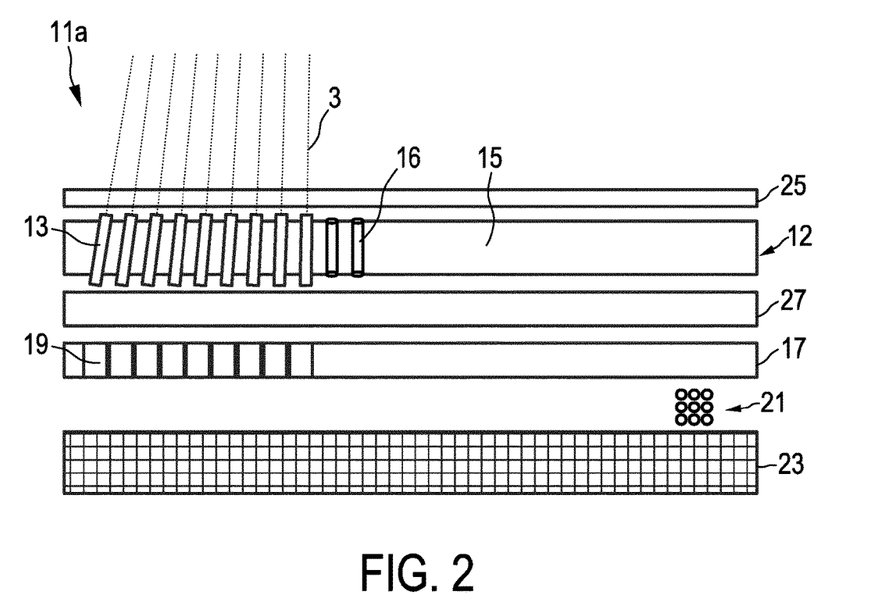
FIG. 2 shows an illustration of an embodiment of a detector according to the present invention.

FIG. 2 shows a schematic illustration of a first embodiment of a detector 11a according to the present invention. The detector 11a comprises a scintillator 12. In the scintillator 12 heavy scintillating fibers 13 (i.e. high-Z inorganic fibers) are used. Such fibers 13 can be produced in a suitable manufacturing process, like the micropulling-down method or ceramic molding processes. The fibers 13 can be grouped in bundles and arranged in order to build a large area detector compatible with single fixed field irradiation (e.g. 40×40 $cm^2$) while keeping a high pixel granularity (e.g. from several hundred microns to some millimeters) on the image plane. The scintillator plane granularity can be customized with the use of different fiber diameters allowing the use of different 2D photosensor arrays depending on the specific application.

The heavy scintillating fibers 13 are held in place by means of a support structure 15. This support structure 15 preferably comprises openings 16 for inserting at least one end of the heavy scintillating fibers 13. The openings 16, i.e. holes, in the support structure 15 can be directed versus the radiation source, such that a fiber 13 (or a bundle of fibers in another embodiment of the detector) of which one end is inserted into an opening is oriented in the direction of the radiation source (not shown, but indicated by the incident radiation 3). Thus, apart from holding the scintillating fibers 13 in place, this support structure 15 also allows giving each scintillating fiber 13 an individual orientation. This individual orientation allows, e.g., constructing a scintillator 12 in focus arrangement, i.e. a scintillator 12 wherein the single scintillation elements (crystals, fibers, etc.) are all directed towards a point or focus point (e.g. the radiation source). This is possible without needing to individually manufacture each scintillation crystal in trapezoidal form. The openings 16 or reflector alveoli provide mechanical support for the fibers 13 and keep them aligned with the beam source, in particular a point source. The thickness of the support structure 15 and the length/depth of the openings 16 can be variable, e.g. accommodating the whole length of the fibers 13 or only a part of it. Preferably, the heavy scintillating fibers 13 are arranged in an array, i.e. a 2D laminar arrangement, wherein each fiber 13 is individually directed to a point source.

The detector 11a further comprises a photodetector 17 for detecting the spatial intensity distribution of the emitted scintillation photons. This photodetector 17 preferably comprises a 1D or 2D array of photosensitive elements 19 allowing the conversion of incident photons into a charge distribution. FIG. 2 further shows an electric interconnect 21 and a data control and support electronics 23, which can be used to read out and further process the charge distribution as detected by the photodetector 17.

The support structure 15 preferably comprises a reflective material in between the heavy scintillating fibers 13 and/or on the inner surface of the openings 16 for providing optical isolation between neighboring fibers. This reflective material can be comprised in the support structure 15 (i.e. the support 15 itself is made from reflective material), deposited on the inner surfaces of the openings 16 in which the heavy scintillating fibers 13 are inserted or also deposited on the heavy scintillating fibers 13 themselves. One effect of this reflective material is that the percentage of scintillation photons generated in a heavy scintillating fiber 13 and conducted to the photodetector 17 can be increased. If there is no reflective material, the generated scintillation photons in one scintillating fiber could migrate to a neighboring fiber before being detected or also leave the scintillator 12 without being detected at all. Restricting the scintillation photons to the fiber by providing a reflective surface between the fibers 13 can thus increase the detection efficiency and/or result in higher accuracy as a higher amount of scintillation photons is detected in or at the end of the scintillating fiber where it was generated.

It is further possible that the detector 11a optionally comprises a reflector 25 covering the heavy scintillating fibers 13 on the side directed to the incident X-ray radiation 3. This reflector 25 can, e.g., be represented by a reflective material deposited on top of the fibers or by a metal plate (comprising, e.g., copper or aluminum) attached to the detector 11, in particular to the support structure 15 of the scintillator 1. The reflector 25 has a similar function as the reflective material between the scintillating fibers 13. Generated photons in one fiber are prevented from leaving the fiber in the direction of the entering radiation. Thus, the reflector 25 is preferably transparent for incident megavoltage X-ray radiation 3 but reflective for generated scintillation photons. For some applications the reflector 25 can be realized by a metal plate that absorbs scatter radiation and acts as a buildup layer besides acting as an optical reflector. By means of the reflective material between the scintillating fibers and the reflector 25 on top of the fibers, a high percentage of scintillation photons generated in a fiber 13 can be restricted to the fiber 13 and appropriately detected by the photodetector.

Still further, there can optionally be comprised an optical layer 27 between the scintillator 12 and the photodetector 17. This optical layer 27 conducts the emitted scintillation photons from the heavy scintillating fibers 13 to the photodetector 17, in particular to the photosensitive elements 19.

In a preferable embodiment of the detector according to the present invention, heavy scintillating fibers of 400 or 800 µm diameter are mapped to a single solid state AMFPI device comprising one hundred or a few hundred square µm photosensitive elements and working in photon counting or integration mode at a specific acquisition frame rate, i.e. counting the scintillation photons per element and time interval. A typical AMFPI device could e.g. have an area of about 40×40 cm² and could e.g. comprise a 1024×1024 array of photosensitive elements (pixels), each pixel covering a 400 µm×400 µm area, or a 512×512 array wherein each pixel covers an 800 µm×800 µm area. Other pixel sizes, number of pixels or areas are possible. The data control and support electronics 23 may comprise a radiation hard FPGA providing data readout, serial formatting, data transmission and control.

Figure 4:
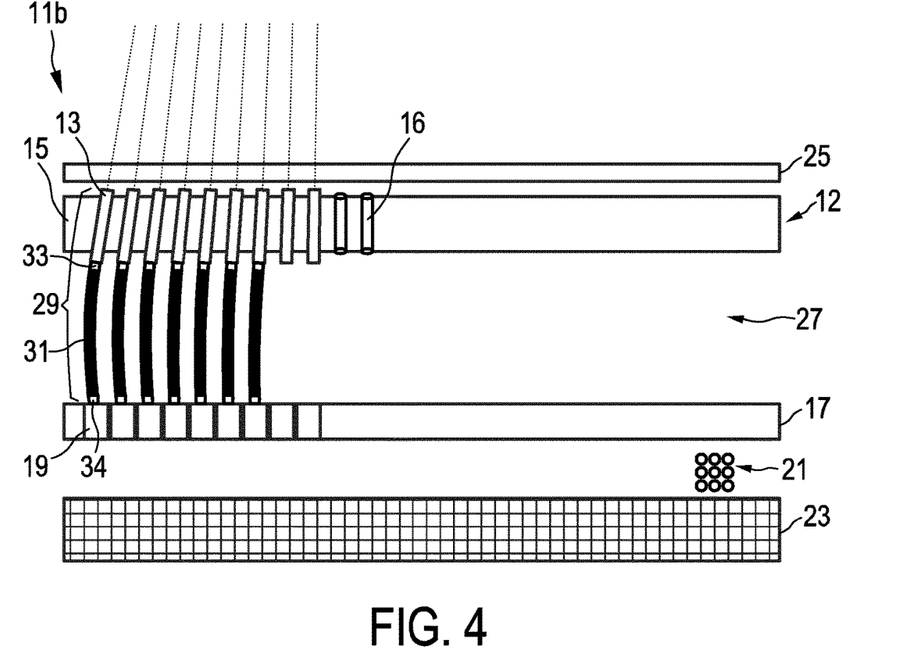
FIG. 4 shows an illustration of another embodiment of a detector according to the present invention.

Alternatively, the optical layer 27 may comprise optical fibers (as illustrated in FIG. 4), in particular flexible optical fibers (standard optical fibers) for conducting the scintillation photons from the scintillator 12 to the photodetector 17.

Figure 3:
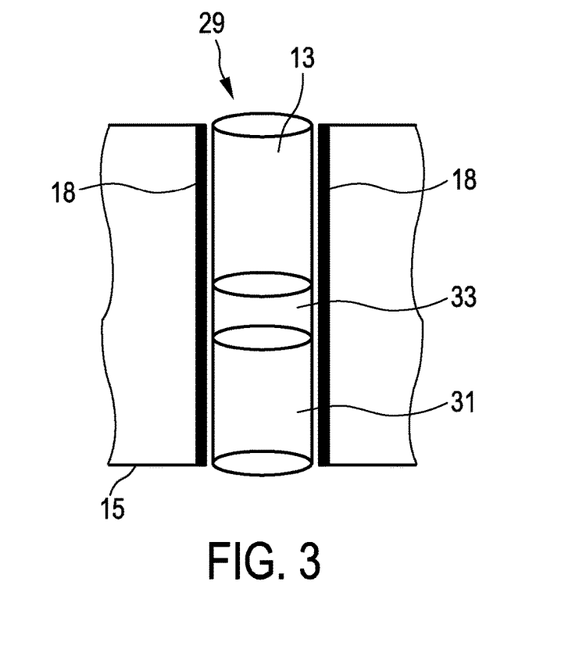
FIG. 3 shows a schematic illustration of a hybrid scintillating-optical fiber.

FIG. 3 illustrates a hybrid scintillating-optical fiber 29, which comprises a heavy scintillating fiber 13 glued to an optical fiber 31 by means of a layer of light conducting glue 33. It is also possible to insert a hybrid scintillating optical fibers 29 into an opening 16 in the support structure 15. In this embodiment, a reflective material 18 deposited on the inner surface of the opening 16 is illustrated. Alternatively, it would be possible to construct the support structure 15 itself from a reflective material. Thus, the optical fibers 31 along with the light conducting glue 33 represent the optical layer 27 in the illustrated embodiment. One advantage of making use of optical fibers 31 in comparison to other possibilities for an optical layer 27 is that a flexible connection between the heavy scintillating fibers 13 and the photodetector 17 can be provided. If, as shown in FIG. 3, one optical fiber 31 is directly connected to a scintillating fiber 13, e.g. by means of light conducting glue 33, it becomes particularly easy to couple the scintillating fibers 13 to the 2D photosensor array, i.e. the photodetector 17.

FIG. 4 shows a further embodiment of the detector 11b according to the present invention comprising such hybrid optical scintillation fibers 29. The fibers are inserted into openings 16 in the support structure 15 thereby held in place. The fibers 29 are arranged in focus arrangement in an array with all fibers 29 directed to a virtual point source (radiation source, not shown in FIG. 4). It is also possible to arrange the heavy scintillating fibers 13 or the hybrid scintillating optical fibers 29 in fiber bundles (not shown) allowing a more efficient manufacturing process, e.g. due to fewer assembly parts. Then, each fiber bundle is directed to the source point, i.e. the radiation source.

Each hybrid scintillating optical fiber 29 comprises a heavy scintillating fiber 13 coupled to a flexible optical fiber 31, e.g. by means of a layer of optical (light conductive) glue 33. Each optical fiber 31 can be coupled to a single photosensitive element 19 in the photodetector 17, e.g. by using a layer of optical glue 34 as well. Alternatively, it would also be possible to detect the scintillation photons in one optical fiber 31 by means of several photosensitive elements, i.e. making use of a photodetector 17 in light-sharing configuration.

The main advantage of such hybrid optical scintillating fibers 29 is that the coupling of the scintillator 12 with the photodetector 17 is flexible. This flexibility can, e.g., allow using a scintillator 12 and a photodetector 17 of different sizes. Also, it is possible to adjust the orientation of the scintillating fibers 13 without needing to alter the design of the photodetector 17. This is particularly useful if the fibers 13 are to be directed to a single point source, i.e. be arranged in focus arrangement. As outlined above, this allows increasing the detection efficiency for high energy, i.e. megavoltage, X-ray radiation by making use of thicker scintillation structures.

Figure 5:
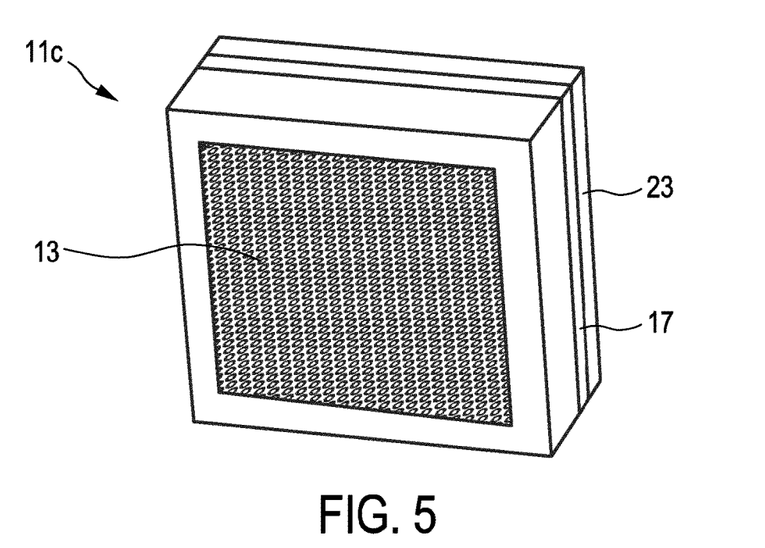
FIG. 5 shows a perspective simplified illustration of a detector according to the present invention.

In FIG. 5 a simplified perspective illustration of an embodiment of such a detector 11c for detecting megavoltage X-ray radiation is shown. It can be seen that one side of the heavy scintillating fibers 13 is open to incident X-ray radiation coming from a radiation source. The heavy scintillating fibers 13 therein are preferably in focus arrangement. Optionally, a reflector (not shown in FIG. 5) could be used to cover the heavy scintillating fibers 13 on the side directed to the radiation source in order to reflect emitted scintillation photons leaving the fibers 13 on this side without being detected by the photodetector 17. The readout and support electronics 23 are usually attached to the side of the detector 11c not directed to the radiation source.

Figure 6:
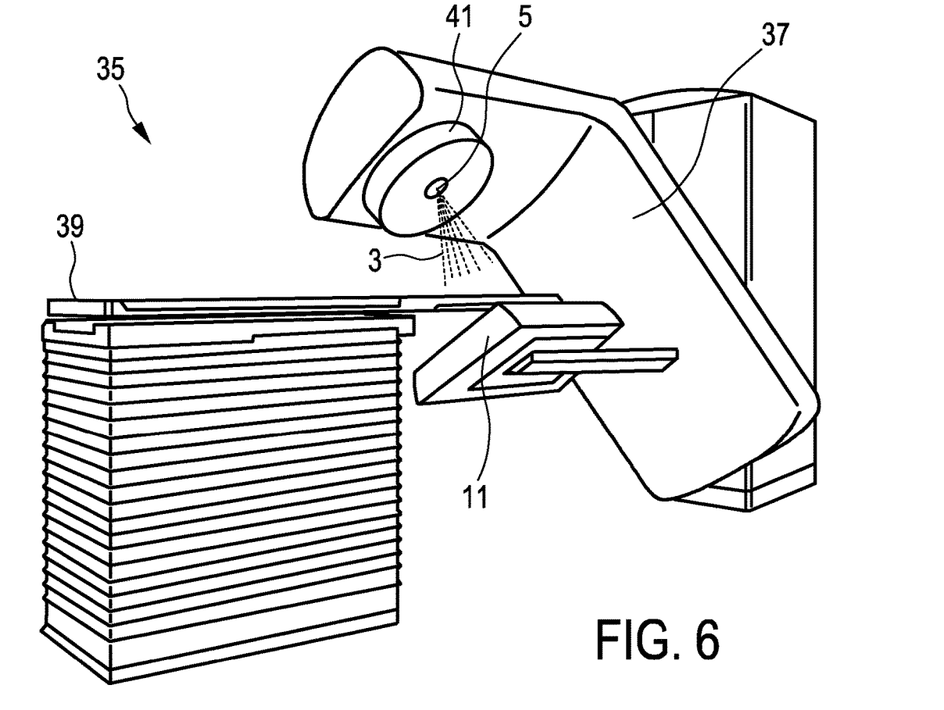
FIG. 6 shows an embodiment of an apparatus for image guided radiation therapy according to the present invention.

In FIG. 6 an apparatus for radiation therapy 35 according to the present invention is schematically illustrated. Most notably, this apparatus comprises a particle accelerator 37 for generating megavoltage X-ray radiation. This particle accelerator is preferably a medical linear particle accelerator (LINAC), which increases the velocity of charged particles by subjecting them to a series of oscillating electric potentials along a linear beam line. The X-ray radiation 3 generated with the LINAC 37, i.e. the treatment beam, is then emitted and directed to a treatment region in a subject or object being subject to treatment. The specific point of emission of the radiation 3 as observed by a patient or object on the subject support can be referred to as radiation source 5.

The apparatus further comprises a subject support 39 for supporting a patient or object being subject to treatment with radiation therapy by use of this megavoltage X-ray radiation. Further, there is comprised a detector 11 for detecting the megavoltage X-ray radiation according to the present invention. In particular, this detector 11 allows detecting high energy, i.e. megavoltage, X-ray radiation, which is used for treatment of a patient or object in radiation therapy.

The apparatus may also comprise beamforming means 41 for expanding or focusing the generated megavoltage X-ray radiation 3 in order to pass through a larger or smaller area of the patient or object on the subject support 39. These beamforming means 41 can be used to influence the shape of the X-ray radiation beam in order to be optimized for imaging or for treatment.

Radiation therapy, as explained above, is often used in cancer therapy. Usually, an apparatus for radiation therapy 35 allows rotating the radiation source 5 in specific angle to allow applying the treatment beam to different areas or volumes in a patient or object being subjected to treatment. One advantage of using the same radiation for treatment and for imaging is that no additional radiation source (i.e. second radiation source) is needed and device costs can be reduced. Further, the construction of an apparatus 35 for radiation therapy can be facilitated as only one radiation generation device has to be included. Still further, compared to an apparatus for radiation therapy comprising a separate imaging modality orthogonal to the direction of the treatment beam, the resolution of the provided images of the treatment fraction in the patient or object being subject to treatment is usually higher if the imaging direction is parallel to the treatment direction.

Figure 7:
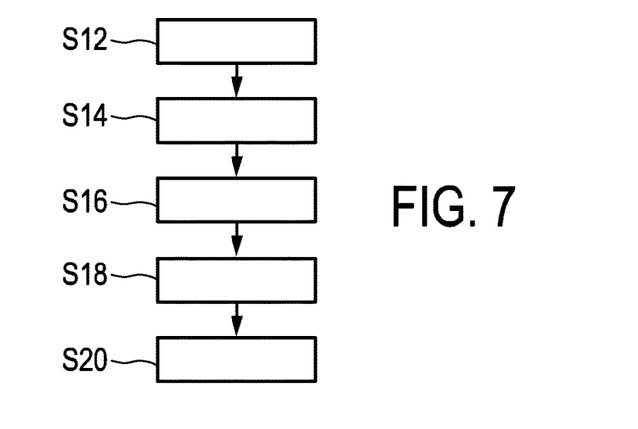
FIG. 7 illustrates a method for detecting X-ray radiation according to the present invention.

An embodiment of a method for radiation therapy according to the present invention is illustrated in FIG. 7. Megavoltage X-ray radiation is generated by a particle accelerator in step S12, usually according to a treatment plan previously computed based on anatomic information of the patient. A patient or object subjected to treatment with radiation therapy by use of said megavoltage X-ray radiation is supported in step S14. The megavoltage X-ray radiation induces the emission of scintillation photons in a scintillator including a plurality of heavy scintillating fibers in step S16. These fibers are held in place during the radiation intrusion in step S18. Then, the spatial intensity distribution of the emitted scintillation photons is detected with a photodetector in step S20. The reconstructed image or projections can be used as input to a reconstruction software that creates a representation of the human body as seen by the irradiation field from the LINAC. This representation can then be compared with the treatment plan and deviations introduced during patient set-up can be identified and corrected if they are above a certain threshold.

According to further aspects of the present invention, it is also possible to only make use of a subset of the steps of the method as described above.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A detector for detecting megavoltage X-ray radiation, comprising
   a scintillator including a plurality of heavy scintillating fibers for emitting scintillation photons in response to incident megavoltage X-ray radiation, said plurality of heavy scintillating fibers comprising an inorganic Z-effective material and pointing in the direction of a radiation source emitting the megavoltage X-ray radiation;
   a support structure for supporting said plurality of heavy scintillating fibers and holding them in place; and
   a photodetector for detecting the spatial intensity distribution of the emitted scintillation photons.

2. The detector according to claim 1, wherein the support structure comprises openings for inserting at least one end of the heavy scintillating fibers.

3. The detector according to claim 1, wherein the support structure holds the heavy scintillating fibers in one or more bundles and/or in an array to be oriented towards a focus point.

4. The detector according to claim 1, wherein the heavy scintillating fibers comprise Ce-doped Lutetium Yttrium Orthosilicate, LSO/LYSO, Ce-doped or Pr-doped Lutetium Aluminum Garnet, LuAG:Ce/LuAG:Pr, Ce-doped Yttrium Aluminium Perovskite, YAP:Ce, Ce-doped Yttrium Orthosilicate, YSO:Ce, Bismuth Germanate, PWO, BGO or GAGG:Ce scintillators in single crystal or ceramic formulations and loaded or unloaded with rare-earth materials like Lutetium.

5. The detector according to claim 1, wherein the support structure comprises a reflective material in between the heavy scintillating fibers and/or on the inner surface of the openings.

6. The detector according to claim 1, further comprising a reflective material covering deposited over the heavy scintillating fibers.

7. The detector according to claim 1, further comprising an optical layer arranged in between the heavy scintillating fibers and the photodetector for conducting the emitted scintillation photons from the heavy scintillating fibers to the photodetector.

8. The detector according to claim 1, further comprising optical fibers arranged in between the heavy scintillating fibers and the photodetector for conducting the emitted scintillation photons from the heavy scintillating fibers to the photodetector.

9. The detector according to claim 8, wherein the optical fibers are flexible for allowing a flexible connection of the heavy scintillating fibers with the photodetector.

10. The detector according to claim 8, wherein each heavy scintillating fiber is connected to an optical fiber by means of light-conducting glue.

11. An apparatus for radiation therapy comprising
   a particle accelerator for generating megavoltage X-ray radiation;
   a subject support for supporting a patient or object being subject to treatment with radiation therapy by use of said megavoltage X-ray radiation; and
   a detector for detecting megavoltage X-ray radiation according to claim 1.

12. The apparatus according to claim 11, wherein the apparatus is configured for simultaneous treatment and detection by use of the same megavoltage X-ray radiation.

13. The apparatus according to claim 11, wherein the particle accelerator is configured to generate pulses of megavoltage X-ray radiation delivering a radiation dose lower than a treatment dose to a patient or object on the subject support and the detector is configured to detect said pulses of megavoltage X-ray radiation.

14. A method for detecting megavoltage X-ray radiation, comprising emitting scintillation photons with an inorganic Z-effective scintillator material configured to scintillate in response to incident radiation, the scintillator material being fashioned into a plurality of heavy scintillating fibers in response to incident megavoltage X-ray radiation, the plurality of scintillator fibers pointing in a direction of a radiation source emitting the megavoltage X-ray radiation;

supporting said plurality of heavy scintillating fibers and holding them in place; and detecting a spatial intensity distribution of emitted scintillation photons in the scintillator fibers with a photodetector.

15. A method for radiation therapy comprising emitting megavoltage X-ray radiation generated by a particle accelerator;

supporting a patient or object that is subject to treatment with radiation therapy by use of said megavoltage X-ray radiation; and detecting said megavoltage X-ray radiation with a method according to claim 14.

16. A detector for detecting megavoltage X-ray radiation from a radiation source, the detector comprising:

a plurality of scintillating fibers of a material with a Z-number greater than 50 and configured to scintillate in response to incident megavoltage X-ray radiation;

a support structure configured to hold the plurality of heavy scintillating fibers with input faces facing a focus point and the scintillating fibers focusing on the focus point; and photodetectors configured to detect light, the photodetectors being optically coupled with output faces of the scintillating fibers to detect light generated by the scintillation generated in the scintillator fibers.

17. The detector according to claim 16, wherein the heavy scintillating fibers comprise Ce-doped Lutetium Yttrium Orthosilicate, LSO/LYSO, Ce-doped or Pr-doped Lutetium Aluminum Garnet, LuAG:Ce/LuAG:Pr, Ce-doped Yttrium Aluminium Perovskite, YAP:Ce, Ce-doped Yttrium Orthosilicate, YSO:Ce, Bismuth Germanate, PWO, BGO or GAGG:Ce scintillators in single crystal or ceramic formulations and loaded or unloaded with rare-earth materials like Lutetium.

18. The detector according to claim 16, further including:

a reflective material between a surface of each scintillating fiber and the support structure.

19. The detector according to claim 16, further comprising:

Flexible optical fibers optically coupling the output faces of the scintillating fibers and the photodetector for conducting emitted scintillation photons from the scintillating fibers to the photodetectors.

20. An apparatus for radiation therapy, comprising:

a particle accelerator for generating megavoltage X-ray radiation;

a subject support for supporting a patient or object being subject to treatment with radiation therapy by use of the megavoltage X-ray radiation; and the detector according to claim 16.

* * * * *